(12) United States Patent
Ahlers et al.

(10) Patent No.: US 9,255,052 B2
(45) Date of Patent: Feb. 9, 2016

(54) METHOD AND SYSTEM FOR PRODUCING METHANOL AND DIMETHYL ETHER

(75) Inventors: Bernd Ahlers, Dietzenbach (DE); Waldemar Liebner, Oberursel (DE)

(73) Assignee: Lurgi GmbH, Frankfurt am Main (DE)

( * ) Notice: Subject to any disclaimer, the term of this patent is extended or adjusted under 35 U.S.C. 154(b) by 532 days.

(21) Appl. No.: 13/379,332

(22) PCT Filed: Jun. 12, 2010

(86) PCT No.: PCT/EP2010/003549
§ 371 (c)(1),
(2), (4) Date: Dec. 19, 2011

(87) PCT Pub. No.: WO2011/000470
PCT Pub. Date: Jan. 6, 2011

(65) Prior Publication Data
US 2012/0101312 A1 Apr. 26, 2012

(30) Foreign Application Priority Data
Jul. 3, 2009 (DE) .......................... 10 2009 031 636

(51) Int. Cl.
C07C 41/18 (2006.01)
B01J 8/00 (2006.01)
C07C 29/80 (2006.01)
C07C 41/09 (2006.01)

(52) U.S. Cl.
CPC ................. *C07C 29/80* (2013.01); *C07C 41/09* (2013.01)

(58) Field of Classification Search
USPC ................................................ 568/698, 699
See application file for complete search history.

(56) References Cited

U.S. PATENT DOCUMENTS

| 4,560,807 | A | * | 12/1985 | Murai et al. | .................. 568/698 |
| 4,744,869 | A | | 5/1988 | Saito et al. | |
| 8,541,630 | B2 | * | 9/2013 | Guo et al. | ...................... 568/698 |

FOREIGN PATENT DOCUMENTS

| CN | 1830934 | | 9/2006 |
| CN | 101412665 | | 4/2009 |
| CN | 101412665 | A * | 4/2009 |
| DE | 1220841 | | 7/1966 |

(Continued)

OTHER PUBLICATIONS

PCT Notification Concerning Transmittal of International Preliminary Report on Patentability from International Application No. PCT/EP2010/003549, corresponding to U.S. Appl. No. 13/381,235, mailed Jan. 26, 2012, pp. 1-12.

(Continued)

*Primary Examiner* — Rosalynd Keys
(74) *Attorney, Agent, or Firm* — Pauly, Devries Smith & Deffner, LLC

(57) ABSTRACT

In the production of purified methanol and/or dimethyl ether from crude methanol, the crude methanol is processed in at least one prepurification stage, a first partial stream of the prepurified methanol is supplied to a final methanol purification and a second partial stream of the prepurified methanol is supplied to a reactor and at least partly converted to dimethyl ether. The dimethyl ether recovered is purified in at least one purification stage, wherein non-reacted methanol is withdrawn from the dimethyl ether purification stage and at least partly supplied to the final methanol purification. In this way, both purified methanol and dimethyl ether can be produced in parallel, wherein the quantities of both products obtained are flexibly adjustable.

13 Claims, 6 Drawing Sheets

(56) References Cited

FOREIGN PATENT DOCUMENTS

| | | |
|---|---|---|
| DE | 102004061352 | 7/2006 |
| JP | 2004161673 | 6/2004 |
| WO | 9628408 | 9/1996 |

OTHER PUBLICATIONS

Changqin, Lin et al., w/English Abstract, "Optimization of Operating State of Pressure column and Atmospheric column in Methanol Three-column Rectification Column", Fertilizer Industry, vol. 32, No. 6, Dec. 28, 2005, 4 pages.

Jie, Huang et al., w/English Abstract, "Discussion on the Double-Effect of the Methanol Three-Column", Medium Nitrogenous Fertilizer, No. 3, May 20, 2004, 3 pages.

Second Office Action for Chinese Patent Application No. 2010800294414 related to co-pending U.S. Appl. No. 13/379,332, mailed Jan. 27, 2014, 27 pages, with English Translation.

* cited by examiner

METHOD AND SYSTEM FOR PRODUCING METHANOL AND DIMETHYL ETHER

CROSS-REFERENCE TO RELATED APPLICATIONS

This application is a national stage application under 35 U.S.C. 371 of International Patent Application Ser. No. PCT/EP2010/003549, entitled "METHOD AND SYSTEM FOR PRODUCING METHANOL AND DIMETHYL ETHER," filed Jun. 12, 2010, which claims priority from German Patent Application No. 10 2009 031 636.1, filed Jul. 3, 2009.

FIELD OF THE INVENTION

The present invention relates to a process for producing purified methanol (MeOH) and/or dimethyl ether (DME) from crude methanol and to a plant for performing this process.

BACKGROUND

Dimethyl ether ($C_2H_6O$, DME) is an ether with two methyl groups as organic residues. High-purity DME is widely used as fuel gas. Due to a cetane number of 55 to 60, dimethyl ether can also be used as a substitute for diesel fuel in a diesel engine. It is regarded as biofuel, if it is made from biomass, and on the long run it should replace liquefied gas. Therefore, DME has considerably gained importance in recent years.

The production of dimethyl ether can be effected by acid-catalyzed condensation of methanol with elimination of water:

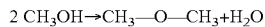

$$2\ CH_3OH \rightarrow CH_3\text{—}O\text{—}CH_3 + H_2O$$

This process for producing dimethyl ether from methanol is described e.g. in "Ullmann's Encyclopedia of Chemistry, Sixth Edition, 1998 Electronic Release". In this process, methanol vapor is passed over a reactor filled with dehydration catalyst, followed by a two-stage distillation. In the first distillation stage, dimethyl ether is recovered as top product, whereas the bottom product chiefly contains non-reacted methanol and product water. This bottom product is separated in the second distillation stage, wherein methanol is withdrawn as top product. The water obtained as bottom product is discarded or used in another process.

For practical reasons, a production of dimethyl ether on a technical scale often is provided directly subsequent to a process for recovering methanol.

For this purpose, WO 96/28408 A1 teaches a process for the production and recovery of dimethyl ether by dehydration of methanol. The energy consumption in the distillation should be reduced in that the bottom product obtained from the first distillation stage is passed over a stripper in which a rough separation of water and methanol is effected. The prepurified methanol stream then is fed into the methanol supply conduit and transferred into a distillation column provided upstream of the dimethyl reactor. As a result, the entire methanol stream fed into the reactor is processed and the purification of the bottom product after the DME reactor is shortened.

In a similar way, JP 2004/161673 A also tries to connect the separation of the product DME from unreacted methanol with a methanol recirculation. For this purpose, the entire crude methanol is purified in a distillation column and subsequently converted to dimethyl ether in a DME reactor. The bottom product obtained in the downstream distillation is recirculated into the crude methanol steam and along with the same into the distillative prepurification.

SUMMARY OF THE INVENTION

The plants described have in common that they are not designed for a simultaneous methanol and dimethyl ether production, but the entire crude methanol is converted into dimethyl ether. However, this leads to the fact that the production of the plant is not able to flexibly react to the requirements of the market in terms of production capacities.

Therefore, it is the object of the present invention to provide a process with which both purified methanol and dimethyl ether can be produced in parallel, wherein the quantities of both products obtained should be flexibly adjustable.

In accordance with the invention, this object is solved with a crude methanol stream processed in at least one prepurification stage wherein the methanol thus prepurified is split up and supplied to a final methanol purification as well as a dimethyl ether production. After the reactor, non-reacted methanol from the dimethyl ether production is withdrawn from at least one purification stage and supplied to the final methanol purification. This allows to variably split up the prepurified methanol stream onto the final methanol purification and the dimethyl ether production, whereby the entire process is rendered more flexible and can be adapted to the current requirements of the market. In addition, plant sections can be saved by combining the distillations.

Since the process of the invention provides for flexibly switching between a 100% methanol production and a 100% DME production, the partial stream supplied to the final methanol purification and to the DME production, respectively, each is understood to be any amount between 0 and 100% in accordance with the present invention.

Advantageously, the prepurification and/or the final purification of the methanol is effected by distillation, as in this way no further substances such as adsorbents or solvents must be introduced into the process in contrast to other separation processes.

In a particularly preferred embodiment, the methanol distillation during the final purification is performed in a column with elevated pressure and/or in a column under atmospheric pressure. In this way, the respective boiling points of the mixture to be separated can be influenced. In the case of a series connection of two columns, i.e. pressure column and atmospheric column, the degree of purity can be adapted to the composition of the substance mixture by thermal separation.

There is furthermore preferred a configuration of the process in which at least parts of the methanol stream withdrawn in the dimethyl ether purification stage are introduced into the pressure column and/or into the atmospheric column. In this way, this methanol quantity likewise can be processed in a value-increasing manner.

Preferably, the purification of the dimethyl ether is effected by distillation, in order to utilize the advantages of a thermal separation process, in particular the absence of additives.

In accordance with the invention, a partial stream of the stabilized methanol stream is utilized to recover non-condensed dimethyl ether after the DME column. Preferably, the stabilized feed methanol is used as washing agent for separating the DME from the low boilers.

In a further preferred configuration of the process at least one partial stream of the methanol is supplied to the prepurified methanol stream intended for the conversion to dimethyl ether after one of the final purification stages. This supply can be effected both before and after a further purification stage and thus provides for a sufficient utilization of the final methanol purification even with a low demand of methanol.

Furthermore, an additional prepurification of the crude methanol is possible in that splitting up the prepurified methanol stream onto the final methanol purification and the dimethyl ether production is performed only after a further purification stage, e.g. the pressure column. As a result, the prepurified methanol stream has a higher degree of purity, which relieves the dehydration reaction and the downstream purification stages.

In accordance with a preferred aspect of the invention, in which the integration of the plant sections is expanded, the gaseous top product of the pressure column is supplied to the DME reactor, wherein the methanol stream can be condensed in addition before entering the DME reactor.

This invention furthermore comprises a plant for producing purified methanol and dimethyl ether from crude methanol, which is suitable for performing the process described above and includes at least one prepurification stage for processing the crude methanol, after which via a suitable system of conduits at least one final purification stage for a further purification of the methanol and at least one dimethyl reactor for converting the prepurified methanol to dimethyl ether are connected with each other in parallel such that both processes can be performed simultaneously. A flexibilization of the plant thereby is achieved in terms of the production capacities of purified methanol and dimethyl ether.

One aspect of the invention provides that a purification stage is provided downstream of the dimethyl ether reactor, in which non-reacted methanol is separated from the ether. This methanol then is supplied through a conduit to at least one of the means for the final methanol purification.

In accordance with a development of the invention both the prepurification of methanol and the final purification of methanol consists of at least one distillation column. This provides for processing the methanol without introducing further substances into the plant.

There is also preferred a configuration of the final methanol purification which includes two columns, one of which is operated under elevated pressure and one under atmospheric pressure, in order to ensure an optimized separation of methanol and water. To minimize the energy consumption, the two columns can be coupled energetically. A heat exchanger preferably is used such that it simultaneously is used as condenser of the pressure column and as evaporator of the atmospheric column, whereby the heat of the top product of the one column is transferred to the bottom product of the other column in an energetically advantageous way. The use of a second evaporator for the atmospheric column is, however, also possible.

In accordance with the invention, a conduit leads from the top of the DME purification column to a purification device, in order to recover non-condensed DME. A configuration of this purification stage as washing column leads to a comparatively low demand of energy in this processing step, but other separating devices likewise are conceivable.

Due to a supply conduit which connects at least one of the devices for the final methanol purification with the dimethyl ether reactor, methanol can additionally be processed to DME, whereas the final methanol purification still is operated above its minimum load.

Further developments, advantages and possible applications of the invention can also be taken from the following description of embodiments and the drawing. All features described form the subject-matter of the invention per se or in any combination, also independent of their inclusion in the claims or their back-reference.

DETAILED DESCRIPTION

Figure 1:
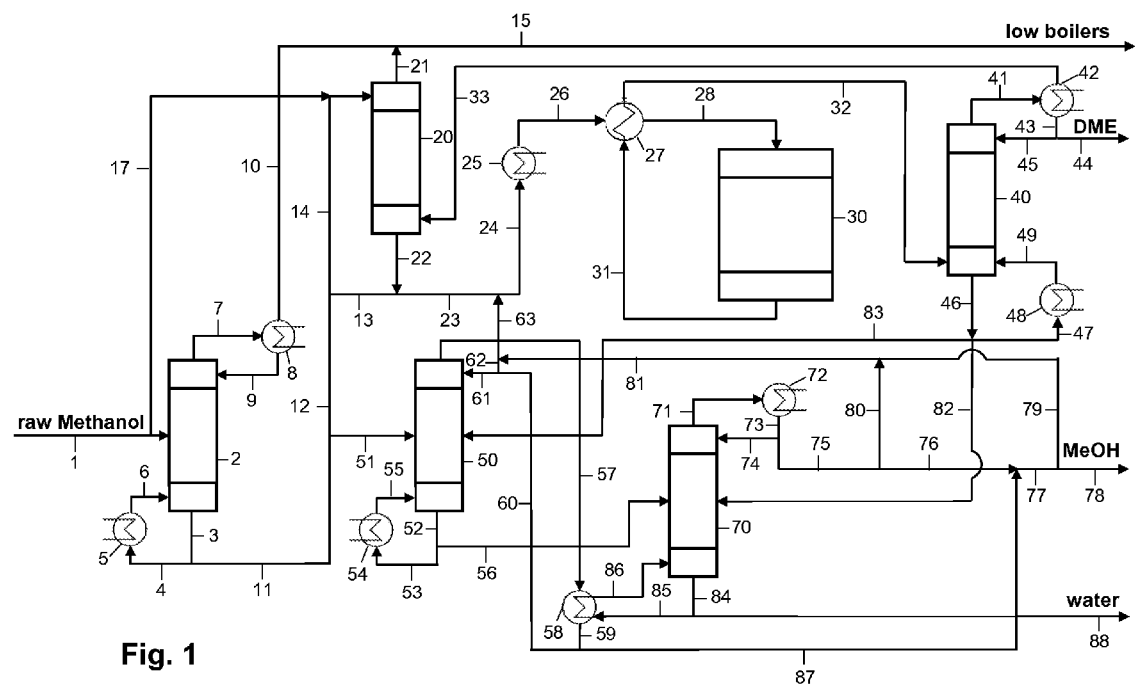
FIG. 1 schematically shows a plant for producing purified methanol (MeOH) and/or dimethyl ether (DME) in accordance with a first embodiment, FIG. 2 schematically shows a plant for producing purified methanol (MeOH) and/or dimethyl ether (DME) in accordance with a second embodiment, FIG. 3 schematically shows a plant for producing purified methanol (MeOH) and/or dimethyl ether (DME) in accordance with a third embodiment, and FIG. 4 schematically shows a plant for producing purified methanol (MeOH) and/or dimethyl ether (DME) in accordance with a fourth embodiment.

FIG. 1 schematically shows a plant for performing the process in accordance with the invention. Via conduit 1, crude methanol (methanol with residual water content) is supplied directly from the production or also from suitable storage devices and prepurified and stabilized in a distillation column 2, from which the vapor in the top of the column is withdrawn via conduit 7 and at least partly liquefied again in a condenser 8. The condensate is recirculated into the column 2 via conduit 9, whereas the distillate consisting of low boilers is discharged from the process via conduit 10. The bottom product is withdrawn from the column 2 via conduit 3 and split up into a product stream and a return stream. The return stream is introduced into an evaporator 5 via conduit 4 and from there returned into the column 2 via conduit 6, whereas the methanol prepurified in this way is discharged as product stream of the column 2 via conduit 11.

Via conduit 51, parts (0 to 100%) of the stabilized methanol stream enter the portion of the plant in which the final methanol purification is performed. Part of the remaining prepurified methanol in conduit 12 (0 to 100%) can directly be supplied to the DME production via conduit 13, whereas via conduit 14 the rest of the methanol stream initially is introduced into a scrubber 20 as washing agent. Alternatively, a partial stream of the crude methanol can directly be supplied to the scrubber 20 via conduit 17 and be available there as washing agent.

Via this scrubber 20, dimethyl ether is recovered from the low boiler stream withdrawn over the top of the DME column 40 by means of a partial stream of the stabilized feed methanol from stream 14 and/or 17, which dimethyl ether was not condensed due to the light ends in the top of the DME column 40 and was recirculated to this point via the stream 33. By means of conduit 21, the low boilers from the scrubber 20 are combined with the stream from conduit 10 and withdrawn via conduit 15. Along with the DME recovered, the methanol stream is withdrawn from the scrubber 20 via conduit 22 and combined with the methanol from conduit 13. Via conduits 23 and 24, the methanol flows into a heat exchanger 25 from which it flows, preferably as vapor, through conduit 26 into a cross-flow heat exchanger 27.

The stream heated further in the cross-flow heat exchanger 27 is introduced via conduit 28 into a dimethyl ether reactor 30. In this DME reactor 30, methanol is continuously converted to dimethyl ether, preferably by acid-catalytic condensation and preferably at a temperature in the range from 150 to 450° C. and a pressure from 1 to 40 bar. Via conduit 31, the product mixture thus obtained is introduced into the cross-flow heat exchanger 27, where it is cooled and at the same time heats the educt stream from conduit 26. Through conduit 32, the cooled product stream is transported to the distillation column 40. Over the top of column 40, the gaseous components are withdrawn via conduit 41, which then are at least partly condensed out in a condenser 42. The liquid components of the stream from conduit 43 are fed back into the column 40 via conduit 45, whereas the product dimethyl ether (DME) is discharged through conduit 44. The bottom product of the column 40 rich in water is withdrawn via conduit 46 and can both be supplied via conduit 47 into the evaporator 48 and from there through conduit 49 back into the column 40 and also via conduits 82, 83 to the final methanol purification, wherein it preferably is supplied to the atmospheric column 70 because of the increased water content. Splitting up onto the two columns 50, 70 is effected such that the quality of the remaining methanol product is maintained. As a result, the non-reacted methanol from the DME production can also be subjected to a value-increasing processing.

Parallel to the DME production, the amount of the prepurified and stabilized methanol which was branched off via conduit 51 is directly supplied to the final methanol purification.

Through conduit 51, methanol therefore is introduced into a pressure column 50, in which the methanol is distilled under an elevated pressure of 5 to 20 bar, preferably 8 bar. The top product of this distillation stage 50 is passed through conduit 57 into the heat exchanger 58 and conduit 59. Via conduit 60, the return flow from the heat exchanger 58 is at least partly recirculated into the column 50 by means of conduit 61, whereas via conduit 62 and conduit 63 the stream can also proportionally be supplied to the feed conduit 24 of the DME reactor 30. The distillate purified to MeOH product quality is discharged via conduit 87. The bottom product of the column 50 enriched with water as compared to crude methanol is withdrawn via conduit 52, split up, and a partial stream is passed through conduit 53 into the evaporator 54, from where this partial stream is returned into the pressure column 50 by means of conduit 55.

Through conduit 56, the remaining methanol stream is introduced into a second column 70, which is operated under atmospheric pressure. Through conduit 84, its bottom product at least partly flows into conduit 85 and from there into the heat exchanger 58, and in partly evaporated form it is recirculated via conduit 86 into the column 70. The remaining portion of the bottom product substantially consisting of water is discharged from the process via conduit 88. It can be introduced into the waste water purification or be reused for example in the generation of synthesis gas. The top product of the column 70 on the other hand is introduced into the heat exchanger 72 by means of conduit 71. The stream emerging from this heat exchanger 72 in conduit 73 is split up such that the return flow is returned into the atmospheric column 70 via conduit 74, whereas the distillate is withdrawn via conduit 75. If required for special operating conditions, the atmospheric column 70 can be equipped with a second reboiler, which can be added in operation with DME production.

From this conduit 75, purified methanol additionally can be introduced into the supply conduit 24 of the DME reactor 30 via the conduits 80, 81 and 63. Via the conduit 76, the purified methanol from the column 70 can also be combined with the methanol withdrawn from the pressure column 50 in conduit 87 and be withdrawn from the plant via the conduits 77, 78. The variability of the process additionally is increased in that a partial stream of the methanol is introduced via conduit 79 into the conduit 81 leading to the DME production. Thus, purified methanol can be fed into the feed stream of the DME reactor 30 both from the pressure column 50 and from the atmospherically operated column 70.

When the top product rich in methanol of the atmospheric column 70 is completely recirculated to the DME production, the atmospheric column 70 can be operated with a reduced return flow, since no methanol product quality is required for the recirculation to the DME reactor 30.

With the plant in accordance with the invention, the amount of methanol and dimethyl ether to be produced can be variable.

When the plant should only produce methanol, the entire stabilized methanol from the forerun column 2 is passed on to the methanol distillation 50, 70. Both in the pressure column 50 and in the atmospheric column 70, methanol product is produced as per specification, whereas in this operating condition no DME is produced. When the plant should produce DME and methanol, a partial stream of the stabilized methanol from the prepurification 2 is passed to the DME reactor 30. The remaining residual stream is passed to the methanol distillation 50, 70. Since the equilibrium turnover of the reaction from methanol to DME is about 80%, the entire stabilized methanol must be passed to the DME reactor 30 for a DME production capacity of 80% of the stabilized methanol. Up to this DME production capacity, the DME reactor 30 can be operated as a once-through reactor, wherein the methanol not reacted in the DME reactor 30 and the process water, i.e. the bottom product of the DME column 40, is passed through the conduit 46 and 82, 83 to the methanol distillation 50, 70 and distilled there to obtain methanol product. The stream withdrawn from the bottom of the DME column 40 via conduit 46 substantially is free from low boilers, which can be adjusted by a corresponding number of trays in the stripping section of the column 40 and/or by the corresponding reflux rate of the column 40. Should other impurities of this stream lead to the fact that the specification of the methanol (preferably Grade AA) cannot be complied with, the methanol must wholly or partly be recirculated to the forerun column 2 via conduits 82 and 83. For optimization of the energy efficiency of the plant it can be expedient to admit a residual amount of DME in the stream of conduit 46. In this case, however, no recirculation from the conduits 82 and 83 is possible, but the entire stream must be passed to the forerun column 2, whereby the amount of DME contained therein is lost.

When the plant should exclusively produce DME, the process water is separated from the bottom product of the DME column 40 in the methanol distillation and the non-reacted methanol is recirculated via the conduit 81 to the DME reactor 30.

In a special embodiment of the invention, methanol product is produced in the pressure column 50, whereas the top product of the atmospheric column 70 is recirculated to the DME reactor 30, and the bottom product of the DME column 40 is exclusively passed to the atmospheric column 70 via the conduits 46, 82. It thereby is avoided that a mass exchange with mass flows of the DME production occurs in the pressure column 50. Correspondingly, the pressure column 50 is operated with the same feed stock as in a pure methanol production.

Figure 2:
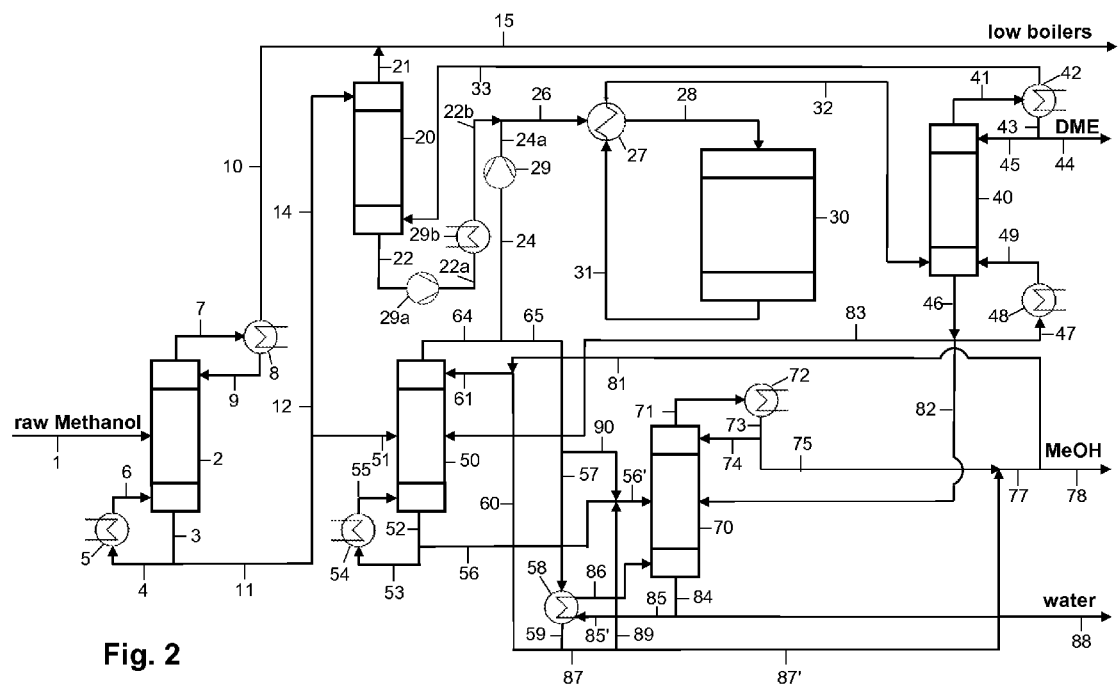

FIG. 2 schematically shows a second embodiment of a plant for performing the process of the invention, in which the integration of both plant sections is expanded. In principle, this embodiment is composed of the same process stages as the plant shown in FIG. 1. In so far, reference is made to the above description and in essence only the existing differences will be discussed.

In the second embodiment, part of the methanol stabilized in the prepurification 2 also is introduced into the scrubber 20 as washing agent for recovering non-condensed dimethyl ether from the top product of the DME column 40. The bottom product containing DME is pumped above reactor pressure by means of a pump 29a, separately evaporated in an evaporator 29b and along with the stream 24a superheated as stream 26 in the heat exchanger 27 and supplied to the DME reactor 30. Thus, Grade AA methanol without DME can be produced in column 50 and column 70.

When not the entire top product of the pressure column 50 is passed into the DME production, the residual stream can be withdrawn as product via conduit 65 and/or at least partly be fed into the inlet 56' of the atmospheric column 70 in gaseous form via the conduit 90 and/or after condensation in the heat exchanger 58 in liquid form via the conduits 59, 87 and 89. The methanol stream rich in water, which is withdrawn from the bottom of the atmospheric column 70 by means of conduit 84, can be recirculated into the bottom of the column 70 via the conduits 85 and 86.

A recirculation of the non-reacted methanol from the bottom product of the DME distillation column 40 is effected via conduit 46, from which both methanol can at least partly be introduced into the pressure column 50 of the final methanol purification via conduit 83 and methanol can at least partly be introduced into the atmospheric column 70 of the final methanol purification via conduit 82.

Due to this configuration of the process, the interaction between final methanol purification and DME production is additionally expanded, wherein the capacity of each component is each designed such that both DME and purified MeOh can be produced at 100%.

The stabilized methanol is completely evaporated in the pressure column 50 and thus the separation of water is completely shifted into this plant section. In addition, the evaporated methanol for the DME production can already completely be passed to the reactor 30, which necessitates, however, that the operating pressure in the pressure column 50 must lie above that of the DME reactor 30. Preferably, the pressure of the pressure column 50 is chosen such that by single-stage compression of the gaseous top product in the compressor 29 the required pressure for forwarding to the DME reactor 30 is achieved. This is satisfied in particular when the pressure column is operated at about 8 bar abs and the reactor 30 is operated at about 16 bar abs. By incorporation of the condenser 29, already existing methanol plants can also be converted for DME production. The evaporator 25 as shown in FIG. 1 can be omitted, since the evaporation is already effected in the column 50.

In an operation of the plant which leads to a 100% production of DME, the methanol recovered from the top of the second, atmospherically operated column 70 also can contain water and therefore is charged as reflux to the pressure column 50 via conduit 81 for further DME production. Since the concentrations of the respective top products and hence the reflux ratios in the two columns 50 and 70 are flexible, they can be adjusted such that their evaporator-condenser coupling is maintained. In addition, a second evaporator can be added to the atmospheric column.

Figure 3:
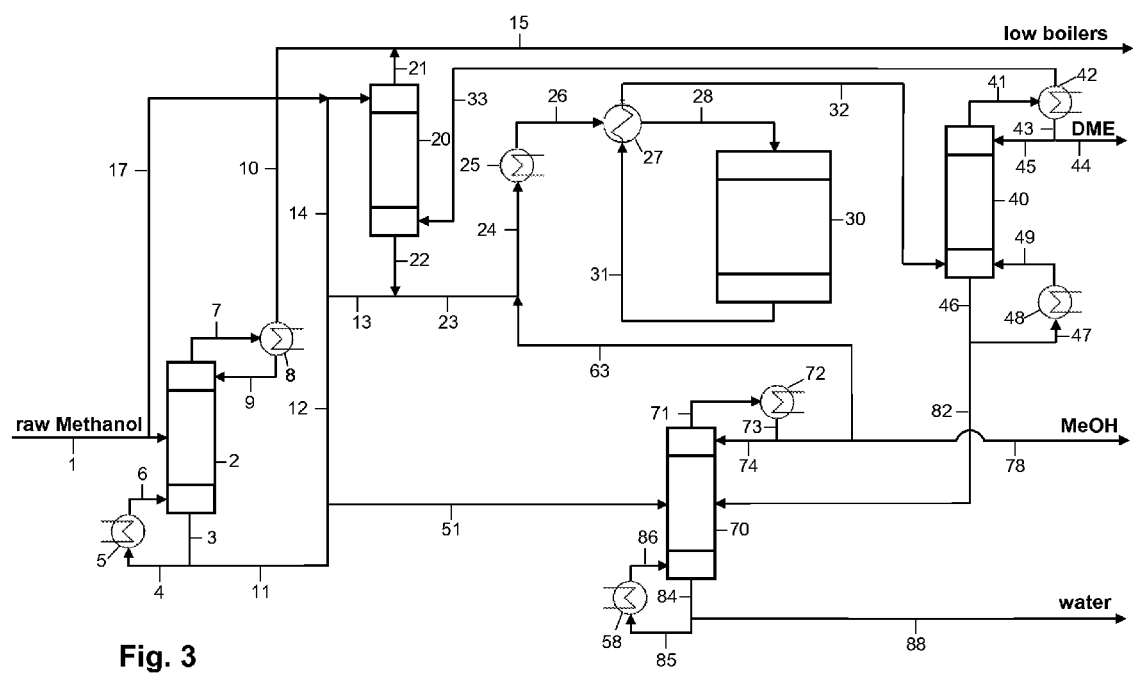

As third embodiment, FIG. 3 shows a plant with a lower methanol capacity. Beside the units for methanol prepurification 2, for recovering DME in the scrubber 20, the DME reactor 30 and for purifying the dimethyl ether thus produced in at least one corresponding apparatus 40, which have already been explained in detail in FIG. 1, only one preferably atmospherically operated column 70 therefore is available for the final purification of methanol. Methanol not reacted in the DME production, can be introduced into the atmospheric column 70 via the conduit 82. The top product of the methanol distillation is withdrawn as product or flows back into the system of conduits of the DME production via conduit 63.

Figure 4:
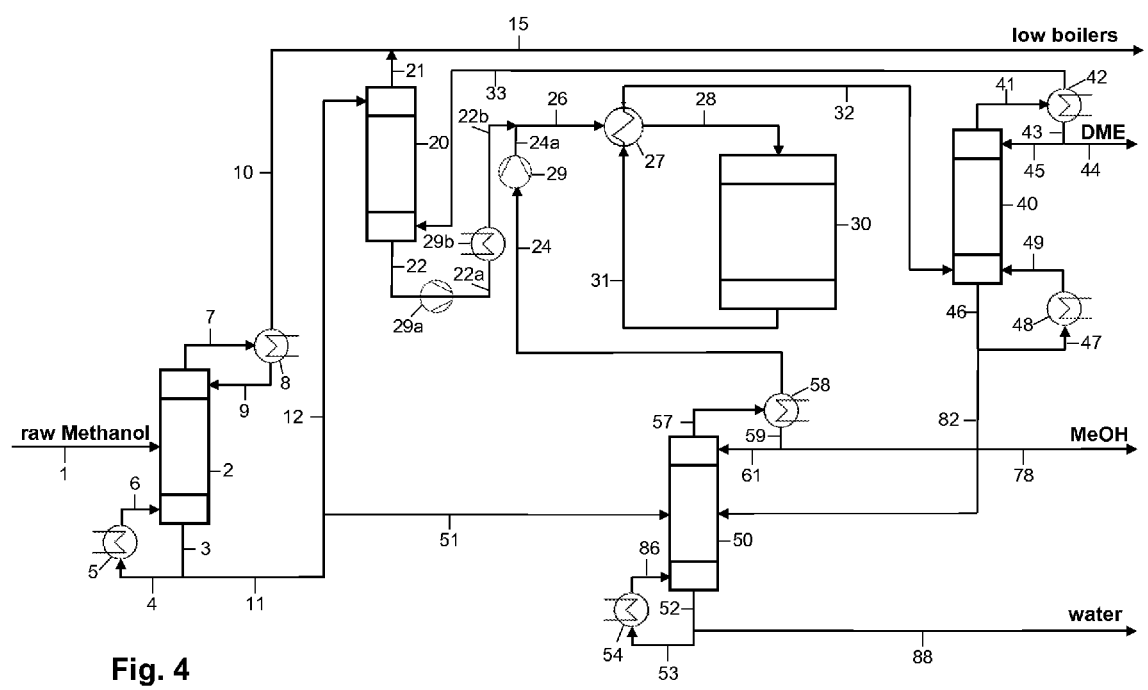
Figure 5:
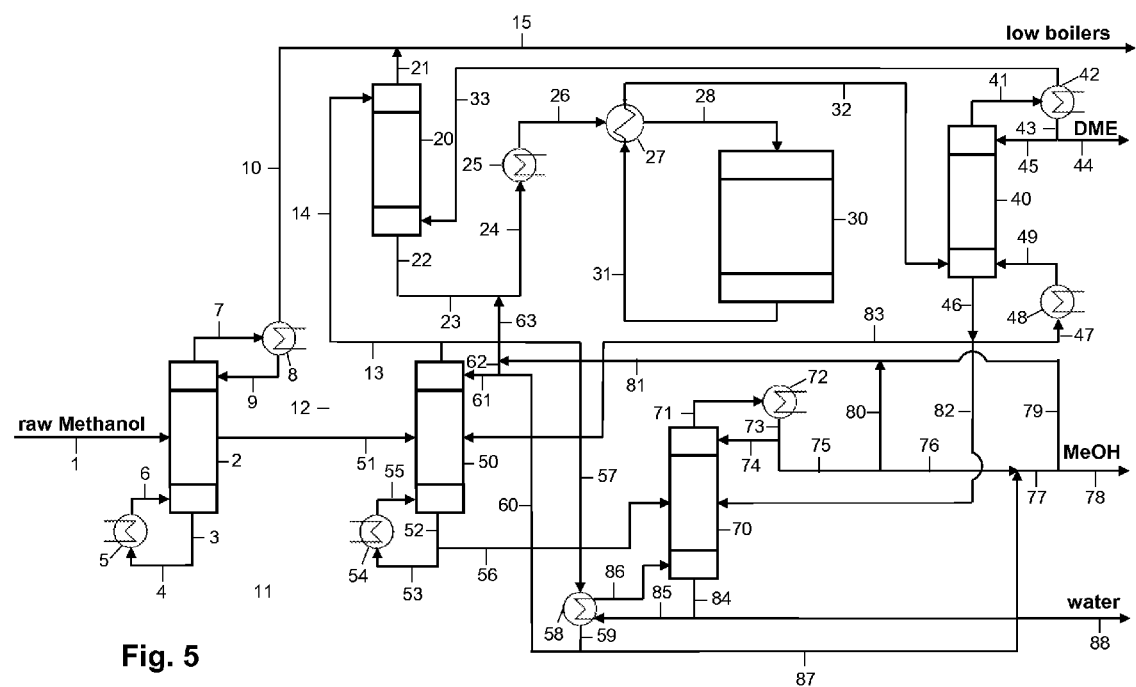
FIG. 5 shows the splitting of the methanol stream onto the final methanol purification columns 50 and 70 and the production of dimethyl ether comprising the scrubber 20 and the dimethyl ether reactor 30 via lines 13 and 57 after the pressure column 50.
Figure 6:
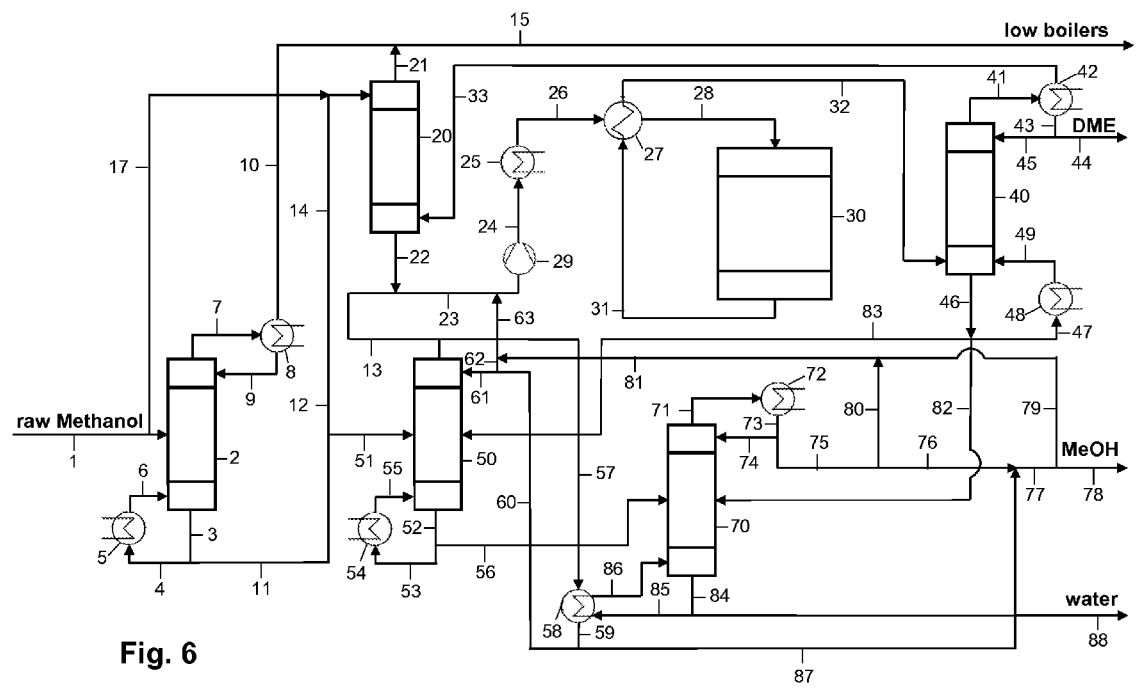
FIG. 6 shows that the gaseous top product of the pressure column 50 is partly fed to the dimethyl ether reactor 30 via line 13, 23, 24, 26 and 28. With condenser 29 between lines 13 and 23, the gaseous top product is condensed before being introduced into the dimethyl ether reactor 30.

Analogous to the process variant shown in FIG. 2, the plant configuration as shown in FIG. 4 is obtained. Here, the final methanol purification likewise is performed with only one column 50, but the same is operated under elevated pressure. This provides for directly feeding the gaseous methanol withdrawn from the pressure column 50 into the DME reactor 30, wherein optionally the use of an additional condenser 29 again is possible. A recirculation of the non-reacted methanol is effected from the DME column 40 via the conduits 46 and 82 into the column 50. In this configuration, like also in FIG. 2, it is possible through conduit 22 to pump the bottom product obtained in the scrubber 20 above reactor pressure, evaporate the same separately and supply the same to the DME reactor 30. As already in the embodiment of FIG. 2, the evaporation of methanol for producing dimethyl ether is also shifted into the column 50. When producing methanol and DME at the same time, the top product of the pressure column 50 must have methanol product quality. Correspondingly, the DME production is operated with pure methanol.

LIST OF REFERENCE NUMERALS 1 conduit
2 MeOH prepurification
3, 4 conduit
5 heat exchanger
6, 7 conduit
8 heat exchanger
9-15 conduit
17 conduit
20 scrubber
21-24 conduit
25 heat exchanger
26 conduit
27 cross-flow heat exchanger
28 conduit
29 condenser
29a pump
29b evaporator
30 DME reactor
31-33 conduit
40 DME purification means
41 conduit
42 heat exchanger
43-47 conduit
48 heat exchanger
49 conduit
50 pressure column
51-53 conduit
54 heat exchanger
55-57 conduit
58 heat exchanger 59-65 conduit
70 atmospheric column
71 conduit
72 heat exchanger
73-77 conduit
78 conduit
79-92 conduit

The invention claimed is:

1. A process for producing purified methanol and/or dimethyl ether from crude methanol, comprising
   processing the crude methanol in at least one prepurification stage,
   supplying a first partial stream of the prepurified methanol to a final methanol purification, and
   supplying a second partial stream of the prepurified methanol to a reactor and at least partially converting the second partial stream to dimethyl ether, and recovering the dimethyl ether and purifying the dimethyl ether in at least one purification stage, and
   withdrawing non-reacted methanol from the dimethyl ether purification stage and at least partially supplying the non-reacted methanol to the final methanol purification,
   wherein the final purification of the methanol is performed in a first column, which is operated under elevated pressure and in a second column which is operated under atmospheric pressure;
   wherein purified methanol from the atmospheric column is fed into the dimethyl ether production.

2. The process according to claim 1, wherein the prepurification of the methanol, the final purification of the methanol, the purification of the dimethyl ether, or a combination thereof is effected by distillation.

3. The process according to claim 1, wherein the methanol stream withdrawn from the dimethyl ether purification stage is at least partially supplied to the pressure column, the atmospheric column, or a combination thereof.

4. The process according to claim 1, comprising recovering dimethyl ether from a gaseous top product of the dimethyl ether purification, by washing with a washing agent rich in methanol.

5. The process according to claim 1, wherein after at least one of the final purification stages at least one partial stream of the methanol is supplied to the methanol stream intended for conversion to dimethyl ether.

6. The process according to claim 1, wherein splitting up a methanol stream onto the final purification of methanol and the production of dimethyl ether is effected after the first column.

7. The process according to claim 1, wherein a gaseous top product of the first column is at least partially supplied to the dimethyl ether reactor.

8. The process according to claim 7, wherein the top product of the first column is condensed before introduction into the dimethyl ether reactor.

9. A plant for producing purified methanol and/or dimethyl ether from crude methanol, comprising
   at least one prepurification stage of the crude methanol,
   at least one final purification stage for final purification of the methanol, and
   at least one dimethyl ether reactor for converting the methanol to dimethyl ether,
   wherein the feed conduits to the final methanol purification and to the dimethyl ether reactor both are connected with the methanol prepurification,
   wherein the final methanol purification comprises two distillation columns, one of which is operated under elevated pressure and one under atmospheric pressure;
   wherein a conduit is provided from which purified methanol from the atmospheric column can be introduced into the supply conduit of the dimethyl ether reactor via conduit.

10. The plant according to claim 9, wherein a dimethyl ether purification stage provided downstream of the DME reactor is connected with at least one final methanol purification stage via a methanol return conduit.

11. The plant according to claim 9, wherein a return conduit from the top of a DME purification column is connected to at least one purification device.

12. The plant according to claim 9, wherein at least one stage of the final methanol purification is connected with the supply conduit of the dimethyl ether reactor.

13. The plant according to claim 11, wherein the return conduit is connected to a washing column.

* * * * *